United States Patent
Woelfert et al.

(10) Patent No.: US 7,112,694 B2
(45) Date of Patent: Sep. 26, 2006

(54) METHOD FOR PRODUCING ISOCYANATES

(75) Inventors: Andreas Woelfert, Bad Rappenau (DE); Christian Mueller, Mannheim (DE); Eckhard Stroefer, Mannheim (DE); Andreas Brodhagen, Dannstadt-Schauernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/513,340

(22) PCT Filed: May 19, 2003

(86) PCT No.: PCT/EP03/05232

§ 371 (c)(1),
(2), (4) Date: Nov. 12, 2004

(87) PCT Pub. No.: WO03/099770

PCT Pub. Date: Dec. 4, 2003

(65) Prior Publication Data

US 2005/0222453 A1    Oct. 6, 2005

(30) Foreign Application Priority Data

May 23, 2002 (DE) ................. 102 22 968

(51) Int. Cl.
*C07C 263/00* (2006.01)
*B01J 10/00* (2006.01)

(52) U.S. Cl. ..................... 560/347; 422/188

(58) Field of Classification Search .............. None
See application file for complete search history.

(56) References Cited

FOREIGN PATENT DOCUMENTS

| DE | 952 086 | 11/1956 |
|----|---------|---------|
| DE | 958 558 | 2/1957 |
| DE | 1 768 439 | 11/1971 |
| DE | 2 112 181 | 10/1972 |
| DE | 31 21 036 | 12/1982 |
| EP | 0 065 727 | 12/1982 |
| EP | 0 322 647 | 7/1989 |
| FR | 1 482 314 | 5/1967 |
| GB | 1 120 770 | 7/1968 |
| WO | 99 40059 | 8/1999 |

*Primary Examiner*—Paul A. Zucker
(74) *Attorney, Agent, or Firm*—Oblon, Spivak, McClelland, Maier & Neustadt, P.C.

(57) ABSTRACT

The present invention relates to a continuous process for preparing isocyanates by reacting primary amines with phosgene, wherein the reaction is carried out in a cascade of at least two tube reactors and the gas phase formed in the reaction is separated off in a phase separator after each reactor and only the liquid phase is passed to the next reactor or to product purification and the reaction volume of the first tube reactor is only a fraction of the total reaction volume.

11 Claims, No Drawings

METHOD FOR PRODUCING ISOCYANATES

The present invention relates to a novel process for preparing isocyanates by reacting primary amines with phosgene in a single-stage reaction in a cascade of reactors provided with facilities for separating off the gas phase between them.

Various processes for preparing isocyanates by reaction of amines with phosgene have been described in the literature.

DE-A-958 558 and DE-A-958 086 describe a two-stage process in which the reactants are passed from the bottom through an upright or obliquely positioned tube in the hot phosgenation, as a result of which phosgene is kept in solution to a greater degree by the pressure of the liquid column in the tube, thus producing a higher phosgene concentration which has an accelerating effect on the reaction. A disadvantage is the poor space-time yield in the cold-hot phosgenation.

DE-A-1 768 439 describes a single-stage phosgenation in a tube reactor in the liquid phase, wherein the temperatures set are so high that the associated hydrochloride is not stable in the solution. A disadvantage is that keeping the phosgene in solution at the temperatures selected requires pressures which are so high that the apparatus becomes very costly. The high temperatures also result in high formation of undesirable by-products.

DE-A-2 112 181 describes phosgenation in cocurrent in a tube reactor packed with random packing, with the flow in the tube reactor being in the transition region between laminar and pulsating flow and part of the finished reaction solution being recirculated to the tube reactor. A disadvantage is the tendency of the reactor to become blocked by deposits on the packing elements.

DE-A-31 21 036 describes a continuous process for preparing isocyanates, in which a constant temperature is maintained over a combination of mixing nozzle and tube reactor. A disadvantage of the process is that the volume of the tube reactor is very large because of the absence of intermediate degassing.

Furthermore, it is known that the use of a large excess of phosgene over the amine used leads to high selectivities to the isocyanate prepared and thus has a decisive influence on the economics of the process. An increasing ratio of phosgene to amino groups tends to increase the phosgene holdup in the plant and the plant volume. However, owing to the toxicity of phosgene, a very small phosgene holdup and a very compact plant construction are desirable. This at the same time results in a reduction in the capital costs of the plant and thus an improvement in the economics of the process.

It is an object of the present invention to provide a process for preparing isocyanates which allows the resulting reactions to be carried out with high selectivity and in a high space-time yield, so that the process can be made geometrically compact.

It has surprisingly been found that the total reaction volume can be reduced compared to the known single-stage process or compared to the multistage process involving cold and hot phosgenation while maintaining the yield of the plant when the reaction is carried out at a single temperature in a cascade of tube reactors and the gas phase formed in the reaction is separated off after each reactor and only the liquid phase is passed to the next reactor or to product purification and the reaction volume of the first reactor is smaller than the total reaction volume divided by the number of reactors.

The present invention accordingly provides a process for the continuous preparation of isocyanates by single-stage reaction of primary amines with phosgene in a cascade of n reactors, where n is a natural number from 2 to 20, wherein the gas phase formed in the reaction is separated off from the reaction mixture downstream of each reactor and the remaining liquid phase is passed to the next reactor and the volume of the first reactor conforms to the following inequality:

$$\text{volume}_{reactor\ 1} < (\text{volume}_{sum\ of\ the\ reactors\ 1\ to\ n})/n.$$

The invention further provides a reaction apparatus for the continuous preparation of isocyanates by single-stage reaction of primary amines with phosgene, made up of a cascade of n reactors, preferably tube reactors, where n is a natural number from 2 to 20, wherein the reactors are provided with a phase separation apparatus suitable for separating off the gas phase formed in the reaction and the phase separation apparatus is integrated into the reactor or is present as a separate vessel and the volume of the first reactor conforms to the following inequality:

$$\text{volume}_{reactor\ 1} < (\text{volume}_{sum\ of\ the\ reactors\ 1\ to\ n})/n.$$

The invention likewise provides for the use of an above-described reaction apparatus for preparing aromatic or aliphatic isocyanates by phosgenation of primary amines.

In a preferred embodiment, n is a natural number from 2 to 5, particularly preferably 2 or 3.

It is also preferred that in the process of the present invention the volume of the first reactor is from 0.1 to 0.9 times, more preferably from 0.3 to 0.85 times, in particular from 0.5 to 0.8 times, the total volume divided by the number of reactors, viz. $[(\text{volume}_{sum\ of\ the\ reactors\ 1\ to\ n})/n]$.

In the preferred embodiment in which n is two, the volume of the first reactor is preferably from 5 to <50%, more preferably from 5 to 45%, even more preferably from 7 to <40%, particularly preferably from 10 to 30%, of the total volume.

The reactors making up the cascade can be any customary reactors which are suitable for continuous phosgenation. Preference is given to using tube reactors.

In a preferred embodiment, the reactors are vertical reaction tubes and the reaction mixture passes through the reaction tubes from the bottom upward.

The tube reactor is preferably heated either via its cylindrical wall or via heating elements present in the tube reactor, e.g. heating coils or heating tubes. To narrow the residence time distribution, the tube reactor can be segmented by means of perforated plates. In a further, preferred embodiment, the tube reactor has a length (L) to diameter (D) ratio L/D of >6, preferably >10. To construct production plants having a high capacity, a plurality of reactor tubes can be connected in parallel.

The process of the present invention is carried out in a single stage. For the purposes of the present invention, this means that mixing and reaction of the starting materials is carried out in one step in a temperature range from 60 to 200° C. In contrast thereto, many processes known from the prior art are carried out in two stages, i.e. mixing of the starting materials is carried out at about 30° C. (carbamoyl chloride is formed in this step, which is often referred to as cold phosgenation) and the mixed starting materials are subsequently heated at from about 120 to 200° C. (the carbamoyl chloride is dissociated to form isocyanate in this step, which is often referred to as hot phosgenation).

In the process of the present invention, the reactants are mixed in a mixing device in which the reaction stream passed through it experiences high shear. As mixing device, preference is given to using a rotary mixing device, a mixing pump or a mixing nozzle which is installed upstream of the reactor. Particular preference is given to using a mixing nozzle.

In a preferred embodiment, the reaction of amine with phosgene is carried out at absolute pressures of from 0.9 bar to 400 bar, preferably from 3 to 35 bar. The molar ratio of phosgene to amino groups used is generally from 1:1 to 12:1, preferably from 1.25:1 to 5:1. The total residence time in the reactors is generally from 10 seconds to 3 hours.

In a preferred embodiment, the separation of the gas phase from the reaction mixture at the end of a reactor is carried out by means of a phase separation apparatus. As phase separation apparatus, it is possible to use an unstirred vessel.

The phase separation can be carried out by means of a phase separation apparatus built into the tube reactor or by means of a separate phase separation apparatus. The phase separation is preferably carried out separately in a vessel which is, for example, configured as an upright or horizontal vessel and in which the separation of the two phases is achieved by calming of the flow through the vessel.

However, it is advantageous in the phase separation for the liquid level to be able to be adjusted according to different load conditions (e.g. partial load). The liquid level can be regulated or unregulated or can be ensured by means of an overflow for separating off the liquid phase. The liquid level is preferably set by regulation. Alternatively, a centrifugal separator can be used for phase separation.

It is also advantageous for the phase separation vessel to be able to be heated/cooled via the wall of the vessel or via heating/cooling devices in the vessel or via an external heat exchanger installed in a circuit connected to the vessel. In this way, cooling of the reaction mixture in the phase separation vessel can be reliably prevented. Cooling could lead to precipitation of sparingly soluble solids from the reaction solution and to blocking of the apparatus.

It has also been found to be advantageous to use pressure reduction devices, preferably pressure-reducing valves, between the phase separation apparatus and the reactors, preferably tube reactors, and/or at the end of the last phase separation apparatus. The pressure maintenance mechanism prevents the phosgene from going prematurely from the reaction solution into the gas phase. It is known that a large excess of phosgene leads to good yields, which would be prevented by the phosgene going over into the gas phase.

To achieve a higher final conversion, it can also be useful for the output from the last reactor of the cascade to be passed to an after-reaction apparatus to allow an after-reaction to occur. As after-reaction apparatus, it is generally possible to use any reaction apparatus in which decomposition of carbamoyl chloride and amine hydrochloride which have not yet reacted in the cascade can occur. Examples of such an apparatus are a distillation column and/or a bubble column. Preference is given to using a distillation column, particularly preferably a reactive distillation column.

In a preferred embodiment, the output is fed into a distillation column in its middle part. Decomposition of the not yet reacted carbamoyl chloride and amine hydrochloride occurs in the column. The liquid phase, for example phosgene, isocyanate, solvent and high boilers, are passed through the column from the top downward and the gas phase, for example hydrogen chloride and phosgene, is passed through it from the bottom upward.

In the after-reaction apparatus, the reaction conditions are generally selected so that decomposition of the not yet reacted carbamoyl chloride and amine hydrochloride occurs. If the apparatus is a distillation column, it is usual to set a pressure which is virtually equal to the pressure in the preceding reactors. The pressure is generally from 1 to 10 bar. The temperature in the distillation column is generally from 60 to 300° C.

As a result of the reduction in the total reaction volume, the plant can be constructed considerably more compactly. In view of the hazardous nature of the phosgene handled in the plant, this considerably increases the safety of the plant and at the same time reduces the capital costs.

In the process of the present invention, it is possible to use any primary amine or a mixture of two or more such amines. Preference is given to using aromatic amines, in particular those of the diaminodiphenylmethane series or their higher homologues. Examples are methylenediphenylamine (individual isomers, an isomer mixture and/or oligomers thereof), toluenediamine, n-pentylamine, 6-methyl-2-heptylamine, cyclopentylamine, R,S-1-phenylethylamine, 1-methyl-3-phenylpropylamine, 2,6-xylidine, 2-dimethylaminoethylamine, 2-diisopropylaminoethylamine, C11-neodiamine, isophoronediamine, 1,6-hexamethylenediamine, naphthylenediamine, bis(3-aminophenyl) sulfone and 4-aminomethyl-1,8-octanediamine.

The process of the present invention is generally suitable for preparing any isocyanates. The process can be employed particularly advantageously for preparing methylene(diphenyl isocyanate) (MDI) and tolylene diisocyanate (TDI).

An additional inert solvent can be added in the process of the present invention. This additional inert solvent is usually an organic solvent or a mixture thereof. Preference is given to chlorobenzene, dichlorobenzene, trichlorobenzene, toluene, hexane, diethyl isophthalate (DEIP), tetrahydrofuran (THF), dimethylformamide (DMF), benzene and mixtures thereof. It is also possible to use the isocyanate which is prepared in the plant as solvent. Particular preference is given to chlorobenzene.

After the reaction, the mixture obtained is preferably separated by rectification into isocyanate(s), solvent, phosgene and hydrogen chloride. Small amounts of by-products which remain in the isocyanate(s) can be separated from the desired isocyanate(s) by means of additional rectification or crystallization.

Depending on the reaction conditions chosen, the product can contain inert solvent, carbamoyl chloride and/or phosgene and can be processed further by known methods (cf., for example, WO 99/40059).

The preferred embodiments described for the process of the present invention apply analogously to the reaction apparatus of the present invention.

The invention is illustrated by the following examples.

EXAMPLE 1

In a coaxial double-tube mixing nozzle, a TDA solution stream consisting of 28.04 kg/h of monochlorobenzene and 7.01 kg/h of TDA, with the TDA consisting of 80% by weight of 2,4-TDA and 20% by weight of 2,6-TDA, was mixed via the inner tube at a velocity of 35 m/s with 56.75 kg/h of liquid phosgene which was introduced via the outer annular gap at a velocity of 15 m/s. The temperatures of the feed streams were set so that the exit stream leaving the mixing nozzle was at a temperature of 100° C. This stream was then passed through a vertical tube having a volume of 2 l (liters) and a length to diameter ratio of 8. The tube wall was maintained at a temperature of 140° C. by external electric heating. At the top of the tube reactor, the liquid phase was separated off from the HCl— and phosgene-containing gas phase. The liquid phase was passed through a further tube reactor having a volume of 10 l and a length to diameter ratio of 8. Here too, the tube wall was maintained at a temperature of 140° C. by means of external electric heating. Once again, the liquid phase was separated off from the HCl— and phosgene-containing gas phase at the top of the tube reactor. After the phosgene and the chlorobenzene had been removed from the liquid phase by distillation, TDI was obtained in a purity of about 99.1% (GC) and a yield of 97% based on the TDA stream fed in. Before and after the synthesis, the apparatus had to be continually flushed with MCB. The total reaction volume was about 12 l. The pressure in the tube reactors was set to 4.5 bar absolute.

EXAMPLE 2 (COMPARATIVE EXAMPLE)

In the coaxial double-tube mixing nozzle of the experimental plant, a TDA solution stream consisting of 28.04 kg/h of monochlorobenzene and 7.01 kg/h of TDA, with the TDA consisting of 80% by weight of 2,4-TDA and 20% by weight of 2,6-TDA, was mixed via the inner tube at a velocity of 35 m/s with 56.75 kg/h of liquid phosgene which was introduced via the outer annular gap at a velocity of 15 m/s. The temperatures of the feed streams were set so that the exit stream leaving the mixing nozzle was at a temperature of 100° C. This stream was then passed through a vertical tube having a volume of 10 l (liters) and a length to diameter ratio of 8. The tube wall was maintained at a temperature of 140° C. by external electric heating. At the top of the tube reactor, the liquid phase was separated off from the HCl— and phosgene-containing gas phase. The liquid phase was passed through a further tube reactor having a volume of 10 l, a length to diameter ratio of 8 and a tube wall temperature of 140° C. Once again, the liquid phase was separated off from the HCl— and phosgene-containing gas phase at the top of the tube reactor. After the phosgene and the chlorobenzene had been removed from the liquid phase by distillation, TDI was obtained in a purity of about 99.1% (GC) and a yield of 97% based on the TDA stream fed in. The pressure in the tube reactors was set to 4.5 bar absolute. Before and after the synthesis, the apparatus had to be continually flushed with MCB. The total reaction volume was about 20 l.

Result: the reaction volume in comparative example 2 was 66.6% greater than in example 1 for the same yield from the process.

EXAMPLE 3

As in example 1, a TDA solution stream consisting of 28.04 kg/h of monochlorobenzene and 7.01 kg/h of TDA, with the TDA consisting of 80% by weight of 2,4-TDA and 20% by weight of 2,6-TDA, was mixed via the inner tube of a coaxial double-tube mixing nozzle at a velocity of 35 m/s with 56.75 kg/h of liquid phosgene which was introduced via the outer annular gap at a velocity of 15 m/s. The temperatures of the feed streams were set so that the exit stream leaving the mixing nozzle was at a temperature of 100° C. This stream was then passed through a vertical tube having a volume of 6 l (liters) and a length to diameter ratio of 8. The tube wall was maintained at a temperature of 140° C. by external electric heating. At the top of the tube reactor, the liquid phase was separated off from the HCl— and phosgene-containing gas phase. The liquid phase was passed through a further tube reactor having a volume of 6 l and a length to diameter ratio of 8. Here too, the tube wall was maintained at a temperature of 140° C. by means of external electric heating. Once again, the liquid phase was separated off from the HCl— and phosgene-containing gas phase at the top of the tube reactor. After the phosgene and the chlorobenzene had been removed from the liquid phase by distillation, TDI was obtained in a purity of about 99.1% (GC) and a yield of 95% based on the TDA stream fed in. Before and after the synthesis, the apparatus had to be continually flushed with MCB. The total reaction volume was about 12 l. The pressure in the tube reactors was set to 4.5 bar absolute.

Result: in comparative example 3, the yield of the process is 2% lower than in example 1 at the same reaction volume.

We claim:

1. A process for the continuous preparation of isocyanates by single-stage reaction of primary amines with phosgene in a cascade of n reactors, where n is a natural number from 2 to 20, wherein mixing and reaction of the starting materials is carried out in one step in a temperature range from 60 to 200° C. and the gas phase formed in the reaction is separated off from the reaction mixture downstream of each reactor and the remaining liquid phase is passed to the next reactor and the volume of the first reactor conforms to the following inequality:

$$\text{volume}_{reactor\ 1} < (\text{volume}_{sum\ of\ the\ reactors\ 1\ to\ n})/n.$$

2. A process as claimed in claim 1, wherein the volume of the first reactor is from 0.1 to 0.9 times [(volume$_{sum\ of\ the\ reactors\ 1\ to\ n}$)].

3. A process as claimed in claim 1, wherein the reactors are reaction tubes.

4. A process as claimed in claim 3, wherein the reaction mixture passes through the upright reaction tubes from the bottom upward.

5. A process as claimed in claim 1, wherein the reaction is carried out in a temperature range from 60 to 200° C. and at absolute pressures of from 0.9 bar to 400 bar and the molar ratio of phosgene to amino groups used is from 1:1 to 12:1 and the total residence time in the reactors is from 10 seconds to 3 hours.

6. A process as claimed in claim 1, wherein the gas phase is separated off from the reaction mixture at the end of a reactor by means of a phase separation apparatus which is integrated into the reactor or is present as a separate vessel.

7. A process as claimed in claim 6, wherein pressure reduction devices are used between the phase separation apparatuses and the reactors and/or at the end of the last phase separation apparatus.

8. A process as claimed in claim 1, wherein the output from the last reactor of the cascade is passed to an after-reaction apparatus in which decomposition of the as yet unreacted carbamoyl chloride and amine hydrochloride occurs.

9. A process as claimed in claim 8, wherein the output from the last reactor of the cascade is fed into a distillation column in its middle part, with the liquid phase being passed through the distillation column from the top downward and the gas phase being passed through it from the bottom upward.

10. A reaction apparatus comprising:
a phase separation apparatus suitable for separating off the gas phase formed by reacting a primary amine with phosgene to produce an isocyanate,
a pressure reduction device, and
a cascade of n reactors, where n is a natural number from 2 to 20,
wherein the volume of the first reactor conforms to the following inequality:

$$\text{volume}_{reactor\ 1} < (\text{volume}_{sum\ of\ the\ reactors\ 1\ to\ n})/n.$$

11. A process for preparing aromatic or aliphatic isocyanates comprising reacting a primary amine with phosgene in the reactor of claim 10.

* * * * *